(12) United States Patent
Hong

(10) Patent No.: US 10,610,239 B2
(45) Date of Patent: Apr. 7, 2020

(54) NON-INVASIVE CEREBRAL PERFUSION INCREASING DEVICE

(71) Applicant: AJOU UNIVERSITY INDUSTRY-ACADEMIC COOPERATION FOUNDATION, Gyeonggi-do (KR)

(72) Inventor: Ji Man Hong, Gyeonggi-do (KR)

(73) Assignee: AJOU UNIVERSITY INDUSTRY-ACADEMIC COOPERATION FOUNDATION, Suwon-si, Gyeonggi-Do (KR)

(*) Notice: Subject to any disclaimer, the term of this patent is extended or adjusted under 35 U.S.C. 154(b) by 0 days.

(21) Appl. No.: 14/397,428

(22) PCT Filed: Apr. 26, 2013

(86) PCT No.: PCT/KR2013/003613
§ 371 (c)(1),
(2) Date: Oct. 27, 2014

(87) PCT Pub. No.: WO2013/162319
PCT Pub. Date: Oct. 31, 2013

(65) Prior Publication Data
US 2015/0094755 A1 Apr. 2, 2015

(30) Foreign Application Priority Data
Apr. 27, 2012 (KR) .................. 10-2012-0044798

(51) Int. Cl.
*A61B 17/135* (2006.01)
*A61B 5/0225* (2006.01)
(Continued)

(52) U.S. Cl.
CPC ........ *A61B 17/1355* (2013.01); *A61B 5/0225* (2013.01); *A61B 5/02225* (2013.01);
(Continued)

(58) Field of Classification Search
CPC .............. A61B 17/1325; A61B 17/132; A61B 17/1322; A61B 17/1327; A61B 17/135;
(Continued)

(56) References Cited

U.S. PATENT DOCUMENTS

| 8,628,490 B2 | 1/2014 | Yacoubian et al. | |
| 2002/0133082 A1* | 9/2002 | Ogura | A61B 5/022 |
| | | | 600/490 |

(Continued)

FOREIGN PATENT DOCUMENTS

| JP | 2001286521 | 10/2001 |
| JP | 2007160088 | 6/2007 |

(Continued)

OTHER PUBLICATIONS

International Search Report for PCT/KR2013/003613, English translation attached to original, Both completed by the Korean Patent Office dated Jun. 26, 2013, All together 5 Pages.

*Primary Examiner* — Tan-Uyen T Ho
*Assistant Examiner* — Chima U Igboko
(74) *Attorney, Agent, or Firm* — Brooks Kushman P.C.

(57) ABSTRACT

A non-invasive cerebral perfusion increasing device including four cuffing pad units and a control unit which is connected to the cuffing pad units and is equipped with a blood pressure sensing module and a compression control module. In the non-invasive cerebral perfusion increasing device each cuffing pad unit respectively includes a compression pad, a compression control member and a blood pressure sensing member. The blood pressure sensing module uses the blood pressure sensing members to sense the systolic blood pressure values of the portions of each of the limbs where they are attached and the compression control module controls the degree of compression of each compression pad by controlling the compression control member to a setting desired by the user based on the sensed blood (Continued)

pressure value, such that the blood flow applied to the limbs is blocked and, indirectly, cerebral perfusion is increased.

4 Claims, 3 Drawing Sheets

(51) Int. Cl.
    *A61B 5/022*     (2006.01)
    *A61B 17/132*     (2006.01)
    *A61B 5/00*     (2006.01)
    *A61B 8/04*     (2006.01)

(52) U.S. Cl.
    CPC ...... *A61B 5/02255* (2013.01); *A61B 17/1325* (2013.01); *A61B 5/6824* (2013.01); *A61B 5/6828* (2013.01); *A61B 8/04* (2013.01)

(58) Field of Classification Search
    CPC . A61B 5/02233; A61B 5/022; A61B 5/02141; A61B 5/021; A61B 5/0205; A61B 5/02; A61B 5/02255; A61B 8/04; A61B 5/6828; A61B 5/6824; A61B 17/1355; A61H 9/0078; A61H 9/0085
    USPC ................................................ 601/148–152
    See application file for complete search history.

(56) References Cited

U.S. PATENT DOCUMENTS

2004/0097817 A1*   5/2004  Nakagawa ......... A61B 5/02007
                                                              600/500
2011/0021927 A1*   1/2011  Sawanoi ............ A61B 5/02255
                                                              600/479

FOREIGN PATENT DOCUMENTS

| JP | 2010527269 | 8/2010 |
| KR | 1020010099155 | 11/2001 |
| KR | 1020070076234 | 7/2007 |
| KR | 1020080096962 | 11/2008 |
| KR | 1020090104917 | 10/2009 |
| WO | 2008065715 | 6/2008 |

* cited by examiner

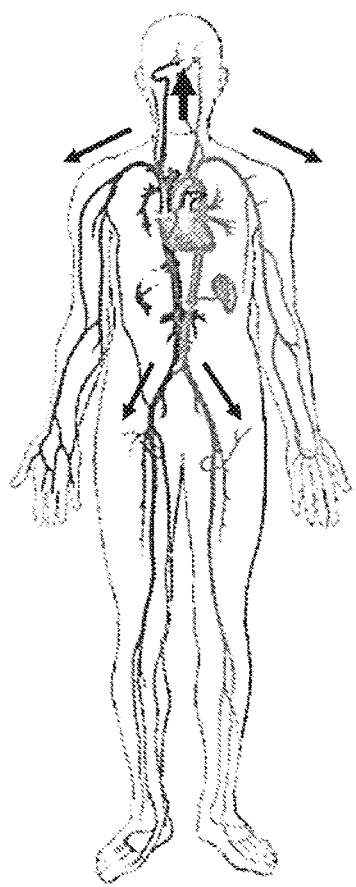
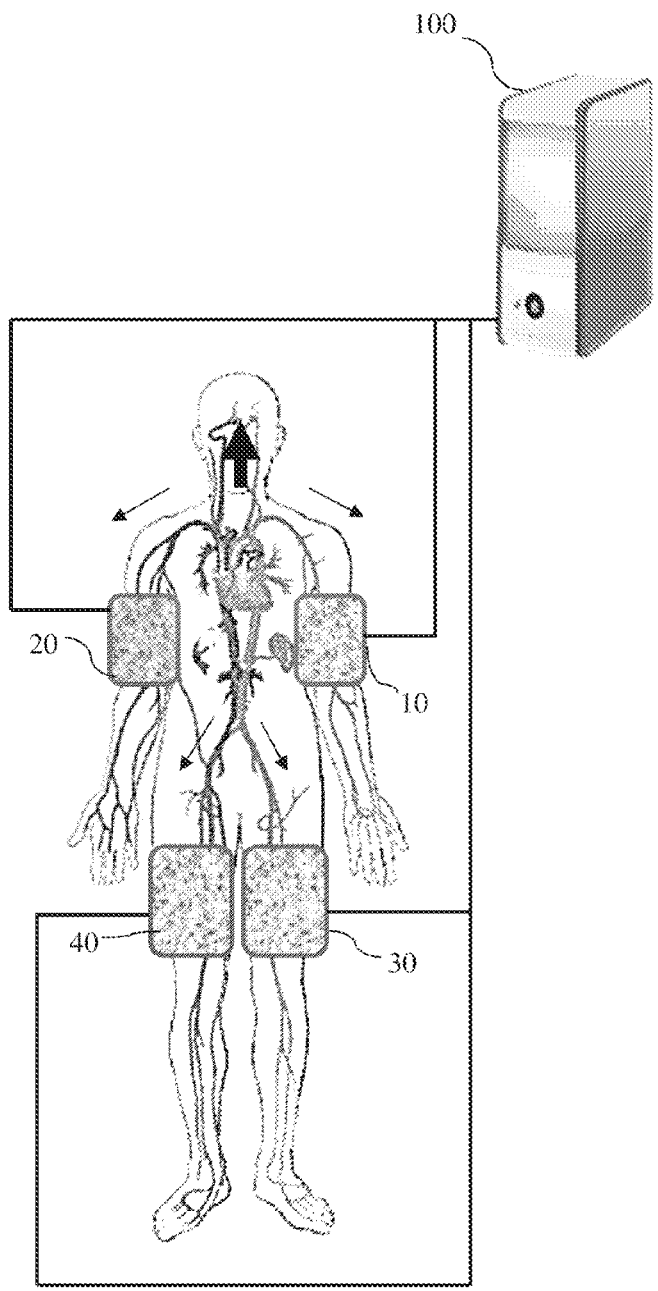
FIG. 1A
FIG. 1B

NON-INVASIVE CEREBRAL PERFUSION INCREASING DEVICE

CROSS-REFERENCE TO RELATED APPLICATION

This application is the U.S. national phase of PCT Application No. PCT/KR2013/003613 filed on Apr. 26, 2013, which claims priority to KR Patent Application No. 10-2012-0044798 filed on Apr. 27, 2012, the disclosures of which are incorporated in their entirety by reference herein.

TECHNICAL FIELD

The present invention relates to a non-invasive cerebral perfusion increasing device that can increase cerebral perfusion in a roundabout manner by compressing the four limbs.

BACKGROUND ART

Ischemic infarction that is caused by the blockade of cerebral blood vessels and vasospasm that is caused by subarachnoid hemorrhage can be partially treated by increasing cerebral perfusion.

However, conventional cerebral perfusion-increasing devices have the problem of causing a plurality of complications because they are used only in an invasive manner.

In order to prevent this problem, the present inventor has devised a cuffing device for compressing arms and legs (hereinafter the "four limbs"), for this, the present inventor has applied compression pads that are generally used in blood pressure gauges.

However, since compression performed to increase cerebral perfusion should continue for a long time, unlike compression by a blood pressure gauge which is only performed for around one minute, problems arise in that a patient suffers from inconvenience due to a serious compression sensation and in that there is concern about the necrosis of the four limbs.

Furthermore, conventional blood pressure gauges take an excessively long time to measure only blood pressure, and thus are not inappropriate for use for a cerebral perfusion increasing device, thus a new scheme for enabling fast blood pressure measurement is required.

Related art documents are discussed below.

When the patented technology disclosed in Japanese Patent Application No. 2007-160088 is practiced, blood flow can be directed toward a head region by inserting a balloon-shaped tube into the main artery and thus partially blocking blood flow directed toward the legs. However, since the invention disclosed in the related art document also uses an invasive method, there is concern about side effects attributable to the inserted catheter.

International Patent Application No. 2008-065715 discloses a similar device. However, this is merely a simple blood vessel diameter measuring device, and thus is unrelated to a device for guiding a blood flow toward the cerebrum and also has associated serious concern about the occurrence of the above-described problem.

(Patent document 1) JP2007-160088 A
(Patent document 2) WO2008-065715 A

DISCLOSURE

Technical Problem

Accordingly, the present invention is intended to overcome the above-described problems and also provide a device that can increase blood flow by compressing the arteries of the four limbs using an external compression device and thus diverting blood to a cerebral region.

Furthermore, the present invention is intended to provide a non-invasive device in order to overcome the disadvantages of invasive cerebral perfusion increasing devices.

In particular, the present invention is intended to provide a device that is capable of achieving a comfortable wearing sensation in any circumstances by taking into account differences in the four limbs of individuals.

Furthermore, the present invention is intended to provide a device that is capable of effectively controlling the level of increase in cerebral blood flow by freely adjusting the level of the compression of the four limbs and the time it takes to compress the four limbs.

Technical Solution

In order to solve the above technical problems, the present invention provides a non-invasive cerebral perfusion increasing device, including four cuffing pad units configured to compress regions of installation; and a control unit connected to the cuffing pad units and configured to include a blood pressure detection module and a compression control module; wherein the cuffing pad units each comprise a compression pad, a compression control member, and a blood pressure detection member; wherein the blood pressure detection module detects the blood pressure value of the corresponding region of installation using the blood pressure detection member; and wherein the compression control module inputs a preset blood pressure value and also controls the compression control member based on the detected blood pressure value, thereby adjusting a level of compression of the compression pad and thus increasing cerebral perfusion in a roundabout manner.

Furthermore, it is preferable that the blood pressure detection member includes a Doppler sensor.

Furthermore, it is preferable that the blood pressure detection member includes a probe attached to the compression pad; and the Doppler sensor is provided inside the probe.

Furthermore, the compression control module should control a pressure value that is used to compress the four limbs. For this purpose, due to the characteristic of blood pressure in that the blood pressure continuously varies depending on the individual or measurement time, it is preferable to measure blood pressure using an accurate sensor each time a measurement is made and then compress the four limbs based on the measured blood pressure.

Furthermore, the compression control module may include the functions of detecting the blood pressure of each of the four limbs using the pad, allowing a user to select a desired condition based on detected systolic blood pressure, and enabling compression of the four limbs at a selected pressure and the release of pressure. This module may include the functions of rapidly operating in accordance with the conditions of a user or a patient and performing repetitive operation. Furthermore, it is preferable that this module controls the compression pad so that the function of adjusting pressure to an appropriate value while the four limbs continue to be compressed can be achieved.

Furthermore, it is preferable that the compression pad is an air tube-type compression pad; and the compression control member controls air that is injected into the air tube-type compression pad.

Furthermore, it is preferable that the compression pad is a gel pad; and the compression control member controls a cubical expansion level of gel inside the gel pad.

Furthermore, it is preferable that the compression pad is a mechanical compression pad in which an air expander is contained; and the compression control member detects and controls oscillation of the expander.

Furthermore, it is preferable that the blood pressure detection member includes a pressure sensor.

Furthermore, it is preferable that the blocking of the blood flow is performed such that pressure is continuously maintained at a uniform value even during the blocking period based on a blood pressure value set in accordance with a systolic blood pressure measured via the pressure oscillation of the pressure sensor within the blocking period.

Advantageous Effects

The present invention provides a non-invasive device, and thus complications that may be caused in an invasive case can be prevented.

In practice, as a result of experiments in which the present invention was applied to 15 normal volunteers, an average 30% of a increasing effect in cerebral perfusion was achieved.

Meanwhile, blood pressure can be detected in real time using a sensor, and a compression level can be automatically adjusted based on this. In particular, the compression level of pads can be freely adjusted in accordance with the unique physical characteristics of a patient, that is, the sizes of the four limbs. Accordingly, the present invention is advantageous in that a patient can be maintained in a comfortable state even when the four limbs are compressed for a long time.

Furthermore, a user can individually set an increase in blood pressure in accordance with a patient, and thus can freely adjust the level of increase in cerebral perfusion based on the state of the patient.

Ultimately, by using a device according to the present invention, the prognosis of acute stroke patients was improved thanks to an increase in a cerebral blood flow.

DESCRIPTION OF DRAWINGS

FIGS. 1A and 1B schematically illustrates a state in which a non-invasive cerebral perfusion increasing device according to the present invention is installed: more specifically, FIG. 1A illustrates a state in which the device according to the present invention is not installed, and FIG. 1B illustrates a state in which the device according to the present invention has been installed;

BEST MODE

The present invention will be described in detail with reference to the accompanying drawings.

Figure 2:
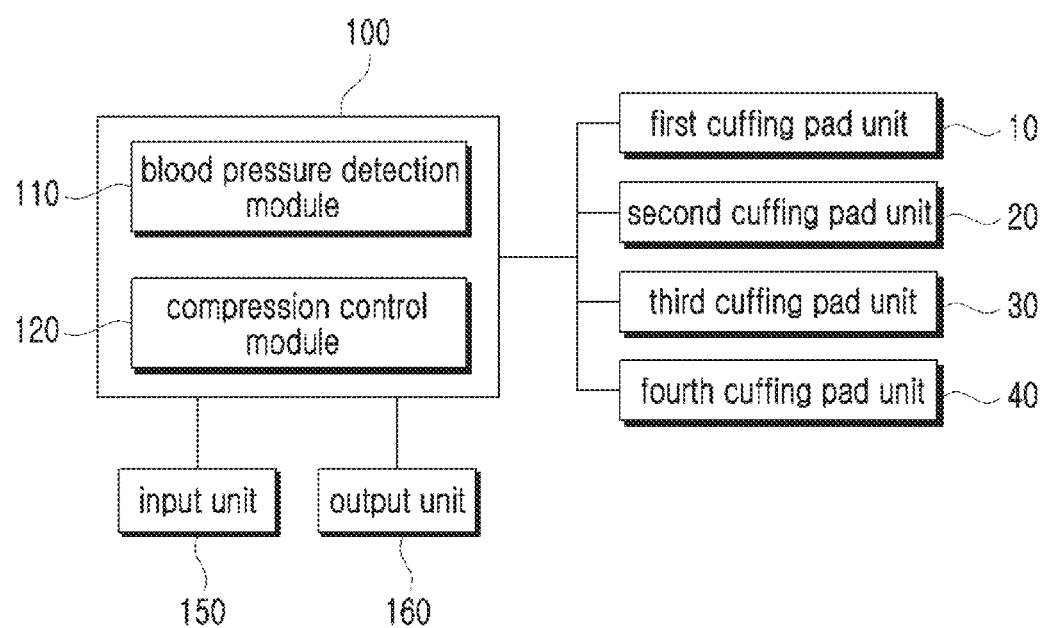
FIG. 2 illustrates a conceptual diagram of a non-invasive cerebral perfusion increasing device according to the present invention.
Figure 3:
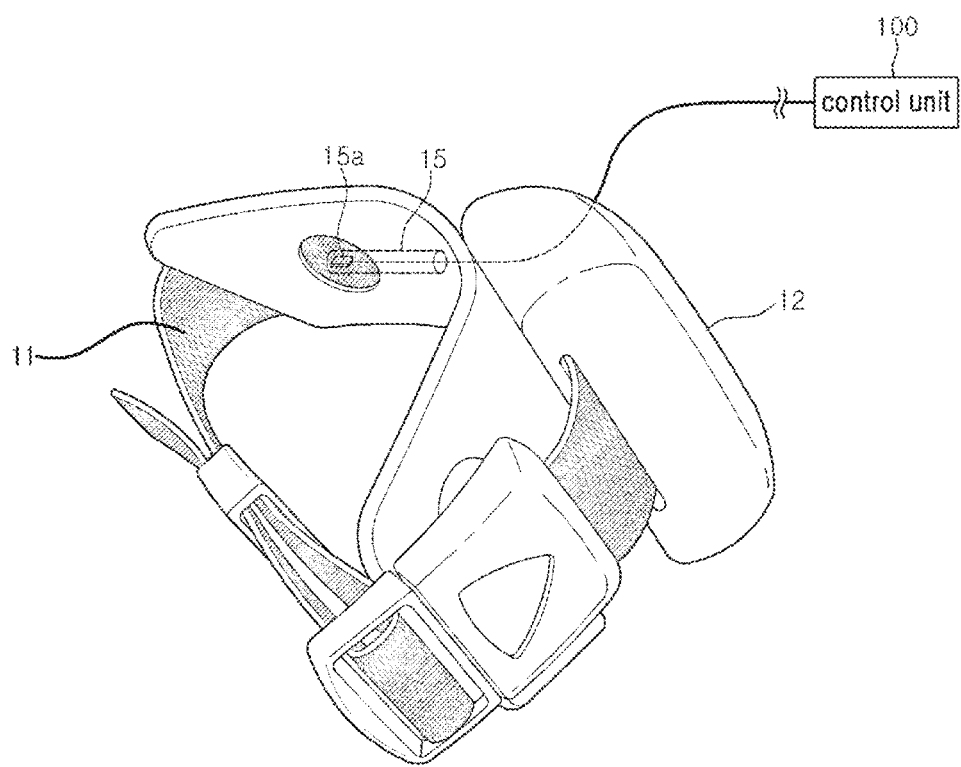
FIG. 3 illustrates any one of cuffing pad units according to the present invention in greater detail.

FIGS. 1 and 2 schematically illustrate a non-invasive cerebral perfusion increasing device according to the present invention, and FIG. 3 illustrates a cuffing pad unit according to the present invention in greater detail.

The non-invasive cerebral perfusion increasing device according to the present invention includes first to fourth cuffing pad units 10, 20, 30 and 40 configured to compress the four limbs, a control unit 100 configured to control the cuffing pad units 10, 20, 30 and 40, an input unit 150 configured to input predetermined information to the control unit 100, and an output unit 160 configured to output predetermined information from the control unit 100.

First, the cuffing pad units 10, 20, 30 and 40 are described in detail with reference to FIG. 3. Although the first cuffing pad unit 10 is taken as an example in FIG. 3 and the following description, it will be apparent that the same structure may be also applied to the second, third and fourth cuffing pad units 20, 30 and 40.

The cuffing pad unit 10 includes a compression pad 11, a compression control member 12 configured to control the compression level of the compression pad 11, and a blood pressure detection member. In this drawing, a probe 15 contained inside the compression pad 11 is illustrated as an embodiment of the blood pressure detection member.

The compression pad 11 is attached around the four limbs and functions to compress the four limbs, and the compression control member 12 functions to adjust the compression level of the compression pad 11 under the control of the control unit 100.

Although the compression control member 12 has been illustrated as being attached to the compression pad 11 in this drawing, the compression control member 12 is not limited thereto. The compression control member 12 may be configured in any structure capable of controlling the compression level of the compression pad 11, and may be installed at any location.

Furthermore, the compression control member 12 can adjust the compression level of the compression pad 11, and thus have the advantage of adjusting the compression level to a value suitable for the physical characteristics of a patient, that is, the unique sizes of the four limbs of a patient.

The compression pad 11 may be any type of pad that is capable of the compressing of the four limbs.

In a preferred embodiment, the compression pad 11 may be an air tube-type compression pad. In this case, the compression control member 12 controls air that is injected into the air tube-type compression pad.

In another preferred embodiment, the compression pad 11 may be a gel pad. In this case, the compression control member 12 controls the cubical expansion level of gel included in the gel pad.

In a still preferred embodiment, the compression pad 11 may be a mechanical compression pad that contains an expander. In this case, the compression control member 12 controls the expander.

The compression pad 11 may be installed on the human body, as illustrated in FIG. 1(*b*).

The blood pressure detection member detects the blood pressure of a portion on which the compression pad 11 has been installed, and then achieves the preferred compression level of the compression pad 11.

A Doppler sensor 15*a* may be used as an example of the blood pressure detection member. This Doppler sensor 15*a* enables the morphological observation of blood vessels in a non-invasive state using ultrasonic waves, via which the degree of a change in blood pressure can be determined using an additional well-known algorithm.

This Doppler sensor 15*a* may be installed in the separate probe 15 attached to the compression pad 11 by a probe reception part outside the compression pad 11.

In this case, the common probe 15 may be used for a plurality of types of compression pads 11 that are separately fabricated in accordance with the different sizes of the four limbs of the individual human bodies.

Furthermore, the compression pad 11 may be fabricated for disposable use. Once treatment over a few hours has been completed, the used compression pad 11 is discarded and a new compression pad is used, thereby a hygienic device being able to be provided.

A pressure sensor (not illustrated) may be used as another example of the blood pressure detection member.

When full air pressure is applied to the cuffing pad unit 10, a flow of blood is eliminated in a corresponding artery blood vessel. Thereafter, when the air pressure of the cuffing pad unit 10 is gradually reduced, blood passes through an initially generated space. At this time, a pulse beats and oscillation occur, and blood pressure may be detected using this phenomenon.

Methods of measuring the blood pressure of the four limbs include a palpation method, an auscultatory method, and an oscillometric method. In the cerebral perfusion increasing device according to the present invention, it is preferable to use a pressure sensor (not illustrated) for rapidly controlling the air of the cuffing pad unit 10 in order to rapidly measure the blood pressure of each of the four limbs and then block a blood flow through each of the four limbs using desired pressure.

The pressure sensor can measure and record the magnitude of pressure oscillation occurring on the cuffing pad unit 10 over an artery blood vessel when air pressure is applied to and then released from the cuffing pad unit 10, measure the blood pressure of each of the four limbs, and allow each of the four limbs to be compressed again using desired pressure.

That is, when the pressure being applied to the cuffing pad unit 10 that has blocked a blood flow through each of the four limbs at a pressure higher than the blood pressure of each of the four limbs of a user starts to be reduced, blood starts to pass therethrough at a specific time. At this time, pressure is applied to the cuffing pad in response to the mechanical motions of the artery of each of the limbs in systolic and diastolic periods, and the pressure sensor of the control unit detects this oscillation. When the pressure being applied to the cuffing pad unit is further reduced, the pressure oscillation of the sensor is also reduced gradually, and ultimately disappears.

In this case, the pressure at a time point when pressure oscillation is initially measured is regarded as systolic blood pressure, and the pressure at a time point when oscillation disappears is regarded as diastolic blood pressure. When a pressure equal to or higher than the systolic blood pressure of each of the four limbs measured based on those physiological reasons is applied to each of the four limbs under the cuffing pad units 10, a blood flow through each of the four limbs can be completely blocked for a specific period.

Furthermore, even while the blood flow through the four limbs is being blocked, compression pressure applied to the four limbs may change due to a change in air pressure within the cuffing pad unit 10. Accordingly, in the present invention, control is performed such that uniform pressure can be maintained.

As another example of the blood pressure detection member, any type of means in which the accuracy of measured blood pressure, the variety of manipulation, the convenience of manipulation, the sanitation of a user, and the variety of functions have been considered may be used.

That is, the present invention may employ a means that eliminates the interference of oscillation or eliminate dynamic noise using an acceleration sensor in order to measure accurate blood pressure, or a means that enables a measurement time to be set for an inpatient or a chronic patient or can manage a plurality of user measurement values in order to manipulate the cerebral perfusion increasing device in various ways.

Furthermore, the present invention may include a means for adjusting a monitor device so that a user can conveniently use the cerebral perfusion increasing device or and may offer convenience to a user, and may employ a means that enables sterilization and disinfection and provides nano silver and perfume in order to provide sanitation to a patient.

Furthermore, in order to allow the functions of the cerebral perfusion increasing device to be diversified, the present invention may be used in conjunction with a health care service system for managing physical information and customized prescription information over a network, may include a means having the functions of calculating average blood pressure and improving a blood flow, or may employ a means that is also used as a step counter or that has a speaking artificial intelligence function.

As described above, the values measured by the blood pressure detection members are transferred to the blood pressure detection module 110 of the control unit 100, and thus an increase in blood pressure compression attributable to the cuffing pad units 10 can be computed.

The above means that may be employed in the present invention correspond to well-known technologies, and thus detailed descriptions thereof are omitted.

Referring back to FIGS. 1 and 2, the control unit 100 is described.

The control unit 100 includes a blood pressure detection module 110 and a compression control module 120.

The blood pressure detection module 110 computes an increase in blood pressure using the blood pressure detection member.

The compression control module 120 performs two functions.

First, upon first installation, the compression control module 120 controls the compression pad 11 so that preferred compression is achieved by controlling the compression control member 12 so that the increase in blood pressure computed by the blood pressure detection module 110 corresponds to a preset increase in blood pressure.

Second, during use after installation, the compression control module 120 allows compression and release to be periodically repeated, rather than continuously maintaining the compression of the compression pad 11. This can achieve an effective increase in cerebral perfusion and also prevent the inconvenience and necrosis of a patient from occurring due to excessive compression.

The input unit 150 may input the preset increase in blood pressure to the control unit 100.

The output unit 160 may output the detected blood pressure to a user.

Furthermore, the control unit 100 may partially block a blood flow directed toward the four limbs, rather than completely blocking it. That is, the control unit 100 may adjust the level of cerebral perfusion by adjusting the pressure of blood flows in the range from 50 to 150% of a measured systolic blood pressure and thus completely or partially blocking blood flows directed toward the four limbs.

Furthermore, the control unit 100 may set the period for which a blood flow is blocked and the period for which a blood flow is allowed. In the present invention, blood pressure should be rapidly measured within a period ranging from 5 to 10 seconds. Accordingly, in this case, in order to reduce blood pressure measurement time, it is preferred that the above-described pressure sensor is used as the blood pressure detection member.

Next, a method of using a non-invasive cerebral perfusion increasing device according to the present invention is described.

A user installs the cuffing pad units 10, 20, 30 and 40 on the four limbs of a patient, and then inputs an increase in blood pressure to be set to the control unit 100 via the input unit 150. The increase in blood pressure to be set is ultimately related to an increase in cerebral perfusion, and thus varies depending the individual state of a patient.

Thereafter, when the user operates the device via the input unit 150, the blood pressure detection members of the cuffing pad units 10, 20, 30 and 40 start to detect an increase in blood pressure attributable to compression.

The blood pressure detection module 110 of the control unit 100 determines whether the detected increase in blood pressure corresponds to the preset and input increase in blood pressure, and then controls the compression control member 12 via the compression control module 120 to achieve the correspondence.

The compression control member 12 additionally presses the compression pads 11, or releases the compression of the compression pads 11. Through this procedure, the compression pads 11 achieve a preset preferable level of compression.

Once initial installation has been completed through the above procedure, the compression control module 120 of the control unit 100 repeats compression and release during the operation of the device. For example, compression and release may be repeated at intervals of 1 minute, but the repetition is not limited to these intervals.

During the above process, the cuffing pad units 10, 20, 30 and 40 compress the four limbs, and thus a cerebral blood flow increases.

When the operation of the device is automatically stopped or is manually stopped by the user via the input unit 150 after an overall preferable period required for use has passed, the control unit 100 releases the compression of the cuffing pad units 10, 20, 30 and 40.

Thereafter, the user releases the cuffing pad units 10, 20, 30 and 40 installed on the four limbs of the patient.

Although the foregoing description has been given with reference to the preferred embodiments of the present invention, it will be apparent to those having ordinary knowledge in the art that variations and modifications may be made to the present invention in various ways without departing from the spirit and scope of the present invention described in the attached claims.

The invention claimed is:

1. A non-invasive cerebral perfusion increasing device, comprising:
    four cuffing pad units configured to compress regions of installation;
    a control unit connected to the cuffing pad units including a blood pressure detection module and a compression control module; and
    an input unit connected to the control unit enabling a user to input a preset increase in blood pressure value to the control unit;
    wherein the cuffing pad units each comprises a compression pad attached around a corresponding region of installation and sized to compress the corresponding region of installation, a compression control member attached to the compression pad and adjusting a level of compression of the compression pad, and a pressure sensor mounted on the compression pad to detect a blood pressure value of the corresponding region of installation;
    wherein the pressure sensor detects the pressure at a time point when pressure oscillation is initially measured, regarded as a systolic blood pressure, when the cuffing pads for compressing the regions of installation start to reduce the pressure from a pressure higher than the systolic blood pressure,
    wherein the compression control module controls the compression control member based on the systolic blood pressure detected by the pressure sensor after the pressure sensor detects the systolic blood pressure;
    wherein the blood pressure detection module determines an increase in blood pressure value at each corresponding region of installation due to compressing of the compression pad using the blood pressure detected by the pressure sensor at the corresponding region of installation,
    wherein the compression control module controls the compression control member so that the increase in blood pressure value computed by the blood pressure detection module matches the preset increase in blood pressure value inputted to the input unit, and then further controls the compression control member so that the compression and release of the regions of installation are periodically repeated after the blood pressure value computed by the blood pressure detection module matches the preset increase in blood pressure inputted to the input unit,
    wherein the non-invasive cerebral perfusion increasing device can increase cerebral blood flow by compressing four limbs through the compression pads.

2. The non-invasive cerebral perfusion increasing device of claim 1, wherein:
    at least one compression pad is an air operated compression pad; and
    the corresponding compression control member controls air that is injected into the at least one compression pad.

3. The non-invasive cerebral perfusion increasing device of claim 1, wherein:
    at least one compression pad is a gel pad; and
    the corresponding compression control member controls the supply of gel to the at least one gel pad.

4. The non-invasive cerebral perfusion increasing device of claim 1, wherein:
    at least one compression pad is a mechanical compression pad; and
    the corresponding compression control member detects and controls oscillation of the at least one mechanical compression pad.

* * * * *